(12) United States Patent
Bartlett, II et al.

(10) Patent No.: US 10,086,120 B2
(45) Date of Patent: Oct. 2, 2018

(54) CONNECTOR FOR COLLECTION AND DISPENSING OF BREAST MILK OR COLOSTRUM

(71) Applicant: LANSINOH LABORATORIES, INC., Alexandria, VA (US)

(72) Inventors: Rush Lloyd Bartlett, II, Moutain View, CA (US); Frank T. Wang, Cupertino, CA (US); Ryan J. F. Van Wert, Palo Alto, CA (US); Jules P. Sherman, Palo Alto, CA (US)

(73) Assignee: Lansinoh Laboratories, Inc.

( * ) Notice: Subject to any disclaimer, the term of this patent is extended or adjusted under 35 U.S.C. 154(b) by 370 days.

(21) Appl. No.: 14/478,713

(22) Filed: Sep. 5, 2014

(65) Prior Publication Data

US 2015/0065996 A1    Mar. 5, 2015

Related U.S. Application Data

(60) Provisional application No. 61/874,303, filed on Sep. 5, 2013, provisional application No. 61/899,482, filed on Nov. 4, 2013.

(51) Int. Cl.
*A61M 1/06* (2006.01)

(52) U.S. Cl.
CPC .................... *A61M 1/062* (2014.02)

(58) Field of Classification Search
CPC ......... A61M 1/06; A61M 1/062; A61M 1/066
See application file for complete search history.

(56) References Cited

U.S. PATENT DOCUMENTS

| 3,911,920 | A | | 10/1975 | Susinn | |
|---|---|---|---|---|---|
| 4,263,912 | A | * | 4/1981 | Adams | A61M 1/06 604/75 |
| 4,323,067 | A | | 4/1982 | Adams | |
| 4,799,922 | A | * | 1/1989 | Beer | A61M 1/06 119/14.49 |

(Continued)

FOREIGN PATENT DOCUMENTS

| EP | 0000339 | 1/1979 |
|---|---|---|
| JP | 2003-299727 | 10/2003 |
| WO | 2014143130 | 9/2014 |

OTHER PUBLICATIONS

Written Opinion of the International Searching Authority, dated Dec. 22, 2014 in PCT Application Serial No. PCT/US14/054377, Dec. 22, 2014, 1-5.

(Continued)

*Primary Examiner* — Bhisma Mehta
*Assistant Examiner* — Matthew A Engel

(57) ABSTRACT

An adapter for use in a system for collecting colostrum and/or milk from a breast may include: a body having a predominantly cylindrical shape; a first open end of the body for connecting to a funnel device; a second open end of the body for connecting to a source of suction; a side port between the first and second ends for connecting to a fluid collection device; a catchment area at or near the side port; and a blocking member between the side port and the second end, for preventing colostrum from passing beyond the side port and through the second end. The blocking member may include at least one aperture for allowing suction force to be transmitted from the second end to the first end.

4 Claims, 5 Drawing Sheets

(56) References Cited

U.S. PATENT DOCUMENTS

| | | | |
|---|---|---|---|
| 4,856,663 A | | 8/1989 | Epp |
| 4,857,051 A | * | 8/1989 | Larsson ............... A61M 1/06 604/346 |
| 4,884,013 A | | 11/1989 | Jackson |
| 4,930,652 A | * | 6/1990 | Murphy ............... B65D 77/283 215/388 |
| 4,961,726 A | * | 10/1990 | Richter ............... A61M 1/0037 604/313 |
| 4,966,580 A | | 10/1990 | Turner |
| 5,531,338 A | | 7/1996 | Sklar |
| 5,542,921 A | * | 8/1996 | Meyers ............... A61M 1/06 604/315 |
| 5,728,137 A | | 3/1998 | Anderson |
| 5,810,772 A | * | 9/1998 | Niederberger ........ A61M 1/06 604/346 |
| 5,941,847 A | | 8/1999 | Huber ............... A61M 1/06 604/74 |
| 5,957,081 A | * | 9/1999 | van der Lely ........ A01J 5/0175 119/14.09 |
| RE36,324 E | | 10/1999 | Yoda et al. |
| 6,023,639 A | | 2/2000 | Hakky |
| 6,200,295 B1 | | 3/2001 | Burchett et al. |
| 6,461,324 B1 | * | 10/2002 | Schlensog ............ A61M 1/06 604/74 |
| 6,471,660 B1 | * | 10/2002 | Covington ......... A61K 49/0004 435/7.23 |
| 6,884,229 B2 | | 4/2005 | Renz |
| 6,966,904 B2 | | 11/2005 | Ruth |
| 7,029,454 B2 | * | 4/2006 | Watanabe ............ A61M 1/06 604/74 |
| 7,048,120 B2 | | 5/2006 | Pond |
| 7,320,678 B2 | | 1/2008 | Ruth |
| 7,648,467 B2 | | 1/2010 | Wang |
| 7,662,127 B2 | * | 2/2010 | Silver ............... A61M 1/064 604/74 |
| 7,875,000 B2 | * | 1/2011 | Krebs ............... A61M 1/06 604/523 |
| 8,052,635 B1 | * | 11/2011 | Kelly ............... A61M 1/0037 604/74 |
| 8,360,102 B2 | | 1/2013 | Khouri |
| 8,979,819 B2 | | 3/2015 | Sherman et al. |
| 8,998,879 B2 | | 4/2015 | Sherman et al. |
| 9,248,077 B1 | | 2/2016 | Kelly |
| 9,623,160 B2 | * | 4/2017 | Alvarez ............... A61M 1/062 |
| 9,642,952 B1 | * | 5/2017 | Kelly ............... A61M 1/0066 |
| 9,782,526 B2 | | 10/2017 | Sherman |
| 2002/0072701 A1 | * | 6/2002 | Nuesch ............... A61M 1/06 604/74 |
| 2002/0156419 A1 | | 10/2002 | Silver |
| 2004/0178162 A1 | * | 9/2004 | Zucker-Franklin ..... A61J 13/00 215/11.1 |
| 2006/0025718 A1 | | 2/2006 | Ostrowski |
| 2007/0118078 A1 | | 5/2007 | McNally |
| 2007/0235405 A1 | | 10/2007 | Fatema |
| 2008/0021380 A1 | * | 1/2008 | Thommen ............ A61M 1/06 604/74 |
| 2008/0039778 A1 | | 2/2008 | Goldie |
| 2008/0255503 A1 | * | 10/2008 | Quackenbush ..... A61M 1/0031 604/74 |
| 2009/0227943 A1 | | 9/2009 | Schultz |
| 2009/0254028 A1 | | 10/2009 | Brittner |
| 2010/0049122 A1 | | 2/2010 | Jaeger-Waldau et al. |
| 2010/0324477 A1 | * | 12/2010 | Paterson ............ A61M 1/0072 604/74 |
| 2011/0054436 A1 | | 3/2011 | Griffis et al. |
| 2011/0168292 A1 | | 7/2011 | Luzbetak et al. |
| 2011/0251552 A1 | | 10/2011 | Brittner |
| 2012/0232524 A1 | | 9/2012 | Hyun |
| 2012/0265169 A1 | * | 10/2012 | Sherman ............ A61M 1/06 604/514 |
| 2013/0005023 A1 | | 1/2013 | Min |
| 2013/0030379 A1 | | 1/2013 | Ingram et al. |
| 2013/0281983 A1 | * | 10/2013 | Sherman ............ A61M 1/06 604/514 |
| 2014/0052106 A1 | * | 2/2014 | Sherman ............ A61J 9/00 604/514 |
| 2014/0135683 A1 | | 5/2014 | Hradisky et al. |
| 2014/0180205 A1 | * | 6/2014 | Lee ............... A61M 1/0023 604/74 |
| 2014/0276629 A1 | * | 9/2014 | Bauer ............... A61M 1/06 604/514 |
| 2015/0065996 A1 | * | 3/2015 | Bartlett, II ............ A61M 1/062 604/514 |
| 2015/0133894 A1 | * | 5/2015 | Sherman ............ A61M 1/068 604/514 |
| 2015/0148783 A1 | * | 5/2015 | Bartlett, II ............ A61M 1/06 604/514 |
| 2015/0283311 A1 | * | 10/2015 | Alvarez ............ A61M 1/0031 604/514 |
| 2016/0331879 A1 | | 11/2016 | Dann |
| 2017/0095600 A1 | | 4/2017 | Sherman |

OTHER PUBLICATIONS

International Search Report, dated Dec. 22, 2014 in PCT Application Serial No. PCT/US14/054377,SONY CORPORATION Dec. 22, 2014, 1-2, Dec. 22, 2014, 1-2.

International Search Report and Written Opinion in PCT/US2013/050464, dated Oct. 24, 2013, 12 pages.

International Search Report and Written Opinion in PCT/US2013/051142, dated Oct. 22, 2013, 11 pages.

International Search Report and Written Opinion in PCT/US2017/065736, dated Mar. 21, 2018, 11 pages.

* cited by examiner

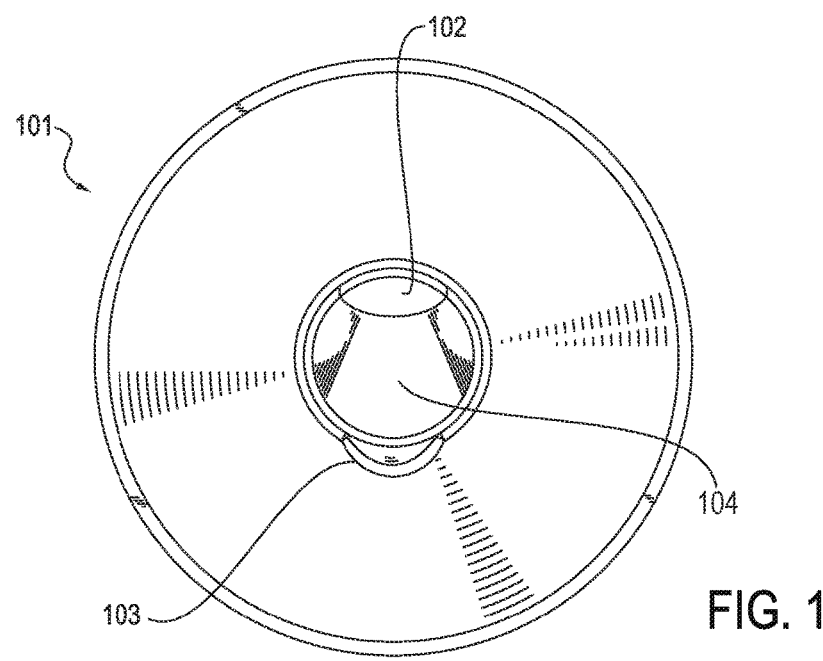
FIG. 1
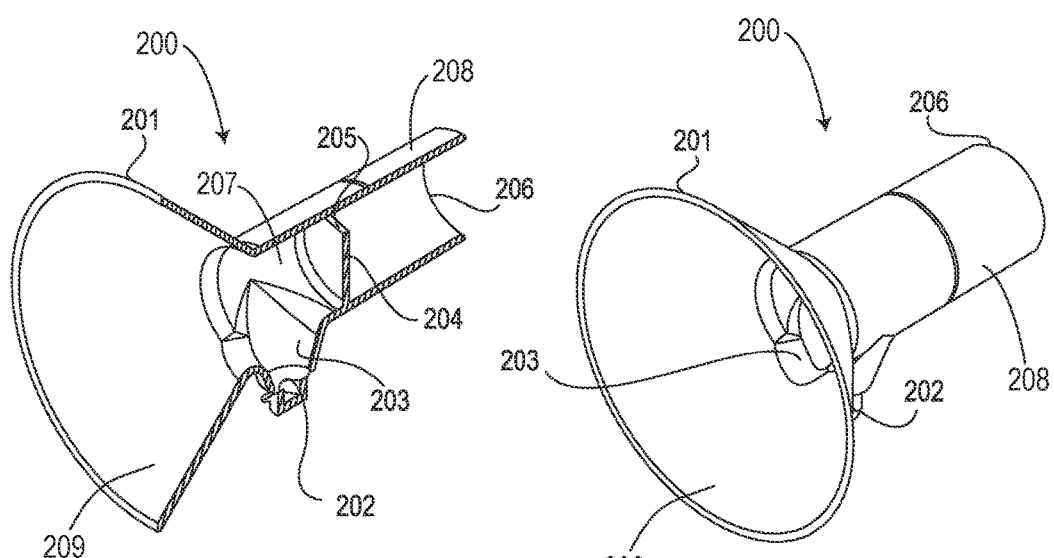
FIG. 2A
FIG. 2B

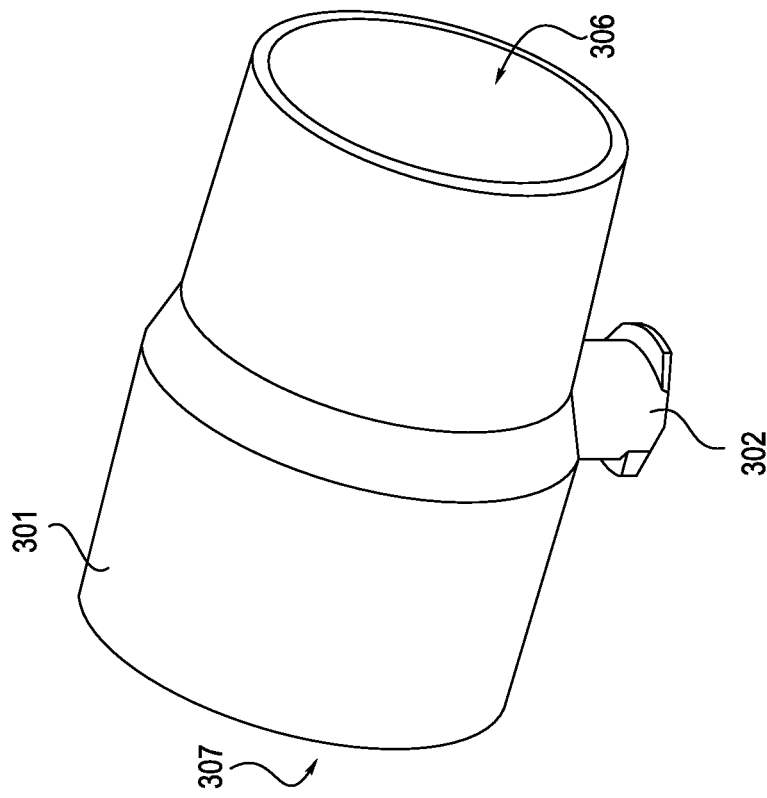
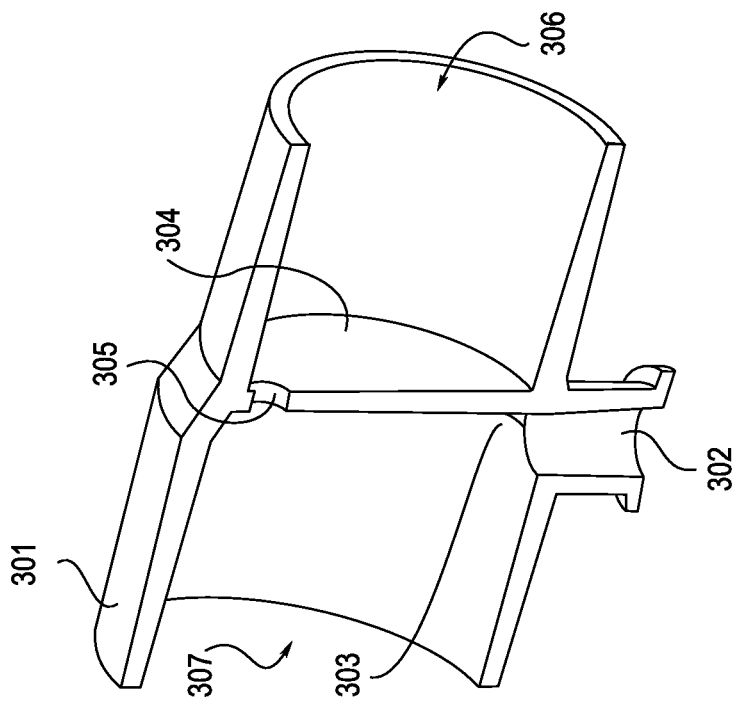
FIG. 3B
FIG. 3A

CONNECTOR FOR COLLECTION AND DISPENSING OF BREAST MILK OR COLOSTRUM

CROSS-REFERENCE TO RELATED APPLICATIONS

This application claims priority to U.S. Provisional Patent Application Nos. 61/874,303, filed on Sep. 5, 2013, and 61/899,482, filed on Nov. 4, 2013. The disclosures of the above-referenced patent applications are hereby fully incorporated by reference.

BACKGROUND

Colostrum is the first nutritional liquid that comes out of the breast during lactation and is a very important food substance for development of a healthy newborn. This highly nutritional material is also packed with antibodies and other immune enhancing substances. Colostrum is produced at a very slow rate of a few millilieters per hour and generally requires some form of pumping and/or hand expression to express it from the breast. Additionally, breast milk sometimes is expressed in small volumes, especially towards the beginning and end of the expression time. Thus, although colostrum is critical for early newborn nutrition, it is only produced in very small quantities and can be difficult to collect.

Currently, colostrum is typically collected using a funnel, also called a breast flange or shield, which connects to a large collection container (such as a milk bottle), typically via a one way valve. Alternatively, hand expression is performed on the breast, and colostrum is collected in a spoon, small cup, or small vial. These collection containers (bottle, spoon, etc.) require transfer to another container—typically a small syringe—for administering small volumes of colostrum to the newborn. This transfer of material from collection container to administration container leads to at least some amount of wasted colostrum, despite the fact that the total collected amount is very small to begin with. The inherent difficulty in collecting and administering colostrum leads many nursing mothers to become discouraged and not collect any colostrum at all. This difficulty also sometimes leads to mothers giving up on breast feeding altogether.

Therefore, it would be advantageous to have improved devices, systems and methods for collecting and administering colostrum. Ideally, such devices, systems and methods would also be applicable for collecting and administering breast milk. Also ideally, such devices, systems and methods would be relatively easy to use and would eliminate the step of transferring colostrum and/or breast milk from a collection container to an administration device. The present disclosure describes various embodiments that meet at least some of these objectives.

BRIEF SUMMARY OF THE INVENTION

The disclosure herein describes an adaptor, a system, and a method for collecting colostrum and/or breast milk from a breast of a female human or animal. In some embodiments, the adaptor, system and/or method may be used for both collection and administration of colostrum and/or breast milk. In general, the adaptor is compatible with a funnel, breast flange/shield, and/or funnel with a flange or connector, such that the connector can facilitate capture and dispensing of breast milk and/or colostrum from a syringe or other compatible collection/administration device. The container, catchment device(s), valves, and connectors may optionally be lubricated, to facilitate the movement of breast fluids, such as colostrum and/or breast milk, into a catchment area. The catchment area collects the fluid and allows it to easily be drawn into, or flow into, a syringe via a connector.

The connector may attach to the front or the rear of a cylindrical syringe with a plunger for expelling material post-capture and/or a plunger for moving to suck or pull material into the barrel of the syringe during capture. The container that is coupled with the adapter to collect colostrum and/or milk does not have to be a syringe, but may alternatively be any container that can connect via a connection means to the funnel adaptor and then expel the material from the same container. This may include, but is not limited to, an attached bag, a vacuutainer, a bottle, a rectangular or odd shaped catchment container, a compressible container, a rollable container, or any other container that can connect to a capture funnel or comprise a capture funnel that also may serve to deliver the material to the infant. A "container" may also be referred to herein as a "fluid collection device," which has a synonymous meaning for the purposes of this application. Thus, a fluid collection device may be any of the types of containers listed above or any other suitable container for use with the adapter and/or system described herein for collection of colostrum and/or milk.

Lubricant or frictional material on the surface of the connectors may serve to facilitate connection to the syringe and or the funnel section or they may serve to allow for rapid flow with less adhesion of the breast product on the wall of the container. This lubricant or frictional material may or may not increase or decrease friction as desired in different regions. Additionally, it may be pressure sensitive through shear thickening or shear thinning It may be silicone, nano-printed with interspaced fluid, or other lubricious or frictionous coating. To increase friction, a sand or imprinted/dimpled area may be used, if desired in connector regions.

The connector for the syringe or other container to the funnel and/or an adaptor that fits both a funnel and a container, may comprise a Luer connector, press fit connector, tapered section, screw thread, tube attachment, or other means of attaching a syringe or other container with an adaptor or funnel that may serve to capture and dispense colostrum.

The funnel and/or adaptor to a funnel may also comprise a catchment reservoir to accumulate droplets of material to or near the connector. The catchment reservoir and surrounding area may optionally be coated with a lubricious material to facilitate movement of material or cause less adhesion to the wall. The catchment area guides the flow of material to the connector when the adaptor or the funnel is in the appropriate configuration. Additionally, a block or guide may serve to facilitate flow into the catchment reservoir, while also including an opening to create a suction force. This opening may be in any area of the block, but one ideal location may in the top half of the block, away from the catchment reservoir side.

Additionally, an adaptor or a funnel may also comprise a system that has two catchment containers of different sizes. In one such example the front container comprising a syringe may be smaller than a back container comprising a bottle or catchment jar. The syringe in the front container may serve to extract small volumes of material where the catchment jar in the back may serve to capture large volumes of materials. The small volume container may be arranged such that it can catch material stopped by a block, while the large container would be filled via the hole in the block that allows for flow into the larger container. There may or may not be a one way valve that helps prevent reverse flow from the larger container and/or flow into the vacuum port in the attachment area of the larger container. This vacuum port in the larger container also comprises vacuum through the hole in the block that is used as a flow-through area to fill the larger container or not used as a flow-through area when the smaller container is desired to be filled. The funnel may be rotated, or a rotational mechanism within the adaptor may be used, if it is desired to keep the funnel stationary if the user wants to switch from extracting small volumes with the syringe to large volumes with the large container. Additionally, the large container could also include attachment means for a syringe or suction port to be used in the catchment area of the funnel or the adaptor.

Also disclosed is a method for capture and dispensing of colostrum or other milk product. A funnel with a connector to a small container or an adaptor to an existing funnel with a connector is used to capture and dispense milk product to an infant. The mechanism of capture is through a funnel, which allows milk product to flow into a catchment area or catchment reservoir. This catchment area or reservoir may or may not be formed by a depression in the side or by the function of a block in the internal section of the opening of the funnel that, when placed on a side orientation, forms a catchment area to collect fluid or viscous material. The block may also have an opening opposite the catchment area, such that air flow or vacuum may facilitate the movement of material out of a breast/nipple. The catchment of the material also comprises a connector that is attachable to a delivery device such as but not limited to a syringe. This delivery device may actively suck up material from the catchment area or may have an opening large enough such that flow from the catchment area into the delivery device can be accomplished with air venting out one or more openings, not excluding the opening forming the connection with the catchment area. The delivery device, once containing captured material, is used to deliver milk product after detachment from the adaptor or funnel with the connector. After detachment, the delivery device is used with a feeding tube or without a feeding tube to administer the milk or colostrum material to the infant or newborn of any species, including but not limited to humans, horses, dogs, cats, hamsters, whales, or any other type of mammal.

In one aspect of the present disclosure, an adapter for use in a system for collecting colostrum and/or milk from a breast may include: a body having a predominantly cylindrical shape; a first open end of the body for connecting to a funnel device; a second open end of the body for connecting to a source of suction; a side port between the first and second ends for connecting to a fluid collection device; a catchment area at or near the side port; and a blocking member between the side port and the second end, for preventing colostrum from passing beyond the side port and through the second end. The blocking member may include at least one aperture for allowing suction force to be transmitted from the second end to the first end.

In some embodiments, the side port is configured to connect to a syringe. In other embodiments, the side port is configured to connect to a tube that connects to a syringe. I still other embodiments, the side port is configured to connect to any other suitable collection device. In some embodiments, the adapter is configured to attach to a breast pump system. In some embodiments, the catchment area comprises a depression in the body adjacent the side port. In one embodiment, for example, the catchment area is a depression surrounding the side port. Some embodiments may also include an additional side port including a valve for switching between collecting colostrum using the side port to collecting milk using the additional side port.

In another aspect of the present disclosure, a funnel device for use in a system for collecting colostrum and/or milk from a breast may include: a body; a funnel shaped portion of the body having a first open end for contacting a breast; a predominantly cylindrical shaped portion of the body having a second open end for connecting to a source of suction; a side port between the first and second ends for connecting to a fluid collection device; a catchment area at or near the side port; and a blocking member between the side port and the second end, for preventing colostrum from passing beyond the side port and through the second end. Again, the blocking member may include at least one aperture for allowing suction force to be transmitted from the second end to the first end. The funnel device may include any of the features described above in relation to the adapter.

In another aspect of the present disclosure, a system for collecting colostrum and/or milk from a breast may include an adapter, a funnel device and a source of suction. The adapter may include any of the features described above. Optionally, the system may also include a syringe, connectable to the side port of the adapter. Alternatively, the system may include a tube, connectable to the side port, and a syringe, connectable to the tube. The source of suction may comprise a breast pump device.

In another aspect of the present disclosure, a method for collecting colostrum from a breast may involve: connecting a funnel device with a first end of an adapter; connecting a suction source with a second end of the adapter; connecting a collection device with a side port of the adapter; contacting an open end of the funnel device with the breast; activating the suction source to generate suction force through the adapter; collecting colostrum in a catchment area of the adapter; and moving the colostrum from the catchment area into the collection device. At least some of these steps may be performed in a different order without departing from the scope of the invention.

In some embodiments, the collection device comprises a syringe, and moving the colostrum from the catchment area into the collection device comprises retracting a plunger of the syringe. In some embodiments, connecting the adapter with a source of suction comprises connecting the second end of the adapter to a breast pump system. Some embodiments may further include collecting milk from the breast through an additional side port in the adapter, into an additional collecting device coupled with the additional side port. Such a method may also further include switching a valve from a first position, for collecting colostrum, to a second position, for collecting milk. The method may also further include preventing the colostrum from passing through the second end of the adapter with a blocking member disposed in the adapter between the side port and the second end.

In another aspect of the disclosure, a method for collecting colostrum from a breast may involve: connecting a small diameter end of a funnel device with a suction source; connecting a collection device with a side port of the funnel device; contacting an large diameter end of the funnel device with the breast; activating the suction source to generate suction force through the funnel device; collecting colostrum in a catchment area of the funnel device; and moving the colostrum from the catchment area into the collection device.

In some embodiments, connecting the funnel device with a source of suction comprises connecting the small diameter end of the funnel device to a breast pump system. Some embodiments may further include collecting milk from the breast through an additional side port in the funnel device or the suction source, into an additional collecting device coupled with the additional side port. Such embodiments may also include switching a valve from a first position, for collecting colostrum, to a second position, for collecting milk. Some embodiments may also include preventing the colostrum from passing through the small diameter end of the funnel device with a blocking member disposed in the funnel device between the side port and the second end.

These and other aspects and embodiments are described in further detail below, in relation to the attached drawing figures.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 is a front view of a collection funnel with a catchment area and blocking element with a suction hole to help form the catchment, according to one embodiment;

FIGS. 2A and 2B are cross-sectional and perspective views, respectively, of a milk and colostrum collection funnel with a catchment area and connector to dispensing device, according to one embodiment;

FIGS. 3A and 3B are cross-sectional and side views, respectively, of a milk and colostrum collection funnel adaptor with a catchment area and connector to a dispensing device, according to one embodiment;

DETAILED DESCRIPTION

Figure 4:
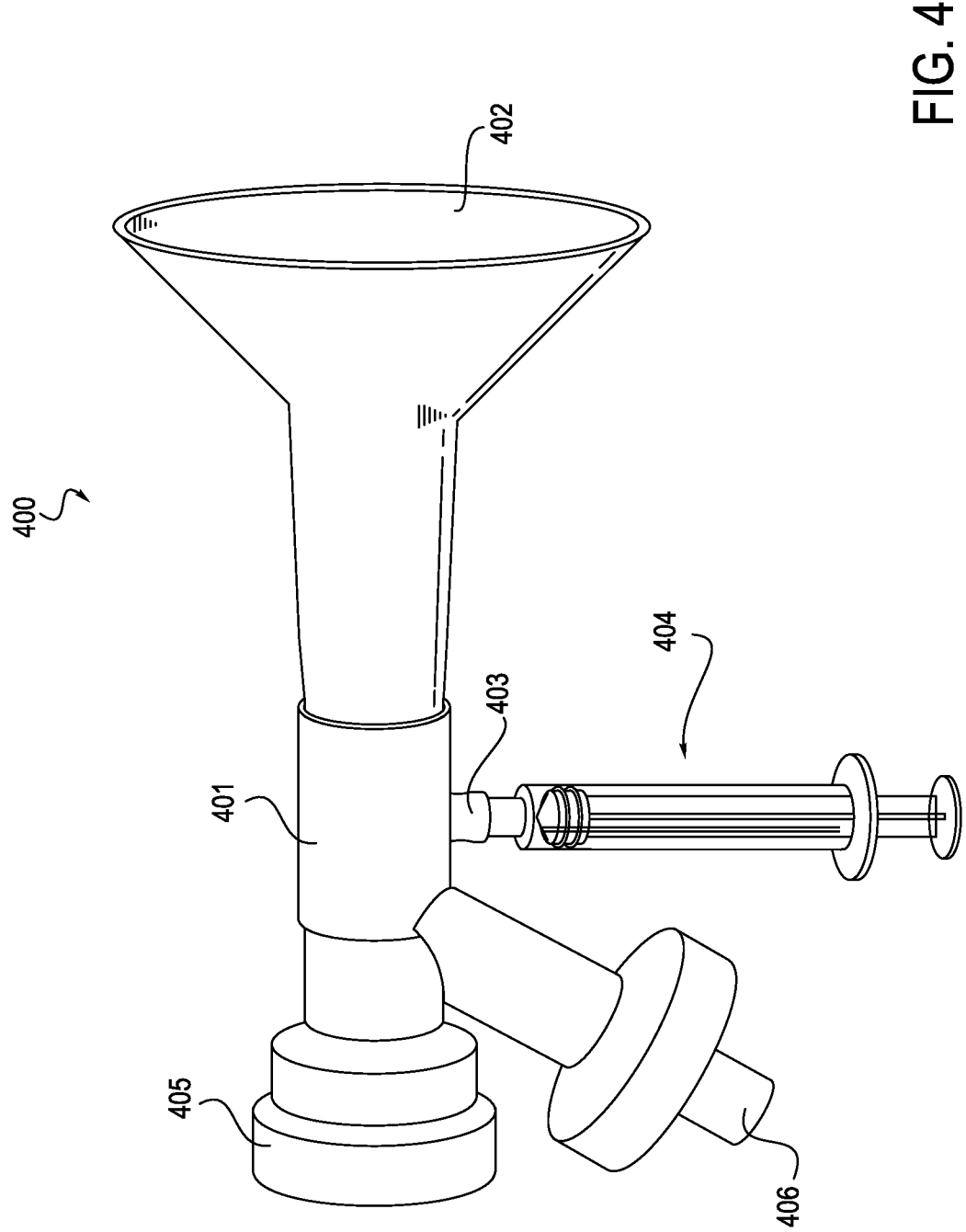
FIG. 4 is a side view of a milk and colostrum collection system with small collection container attachment and large collection container attachment, according to one embodiment.

All figures either depict components in isolation or with breast pump accessory attachments or funnels, for use with a vacuum style breast milk pump that is hand powered or machine powered. The system is operable with suction and attachment to a breast to express the milk or colostrum through a funnel contacted to the breast. Embodiments allow for the capture of colostrum or milk into a collection device, which is then detached from the remainder of the system in order to deliver the milk or colostrum to the newborn, infant, or baby. In various exemplary embodiments, the components of a device or system may be press fit together, glide, screw in, or otherwise attach. In addition, in some embodiments, some components may rotate or glide and experience varying degrees of frictional resistance.

FIG. 1 depicts an exemplary funnel (101) for capture of milk or colostrum. The funnel (101) includes a block (104) with a hole (102). The block (104), in addition to, or in absence of, an indentation (103) serves as a catchment area, which concentrates and guides milk or colostrum to a connector that facilitates transfer into a delivery device, such as a syringe.

FIGS. 2A and 2B depict an exemplary funnel device (200) with a funnel shaped portion (209) having a first open end (201) for contacting a breast, a cylindrical portion (208) having a second open end (206) for connecting to a source of suction, and a catchment reservoir (207) between the two ends that is at least partially formed by a depression (203), a connector (202) meant for connection to a delivery device, such as a syringe, and a block (204) with a vent hole (205). The connection of the connector (202) to the syringe can be made through a luer connector, screw connector, press fit connector, or a hybrid of two or more connection mediums comprising multi-connector functionality to work with multiple delivery devices.

FIGS. 3A and 3B depict an embodiment of an adaptor (301), which includes a front connection (307) to a collection mechanism, such as a funnel, and a rear connection (306) that connects to a flow driver source such as a vacuum pump. The adaptor also comprises a connector to a delivery device (302) and a catchment area (303) that is at least partially formed by a block (304) that has a partial opening or hole (305) that allows for flow force such as suction to pass through.

FIG. 4 depicts an exemplary side view of an embodiment of a system (400) to collect and dispense milk or colostrum using a funnel (402) with a connector or with an adaptor (401) comprising a connector (403) to a delivery device (404). The system (400) has a port to allow for a flow force such as vacuum (405) and it may or may not have a one way valve (406) or an attachment for a larger container. The smaller delivery device (404) may be used to collect small quantities of liquid or more viscous liquid such as but not limited to colostrum, or it may be used to periodically sample small quantities from the flow stream into the larger container. Additionally the delivery device (404), if prefilled with air before attachment, may be used to force air into the funnel section (402) in order to build positive pressure that would facilitate the detachment of the breast from the suction of the funnel (402) by neutralizing the vacuum force. The delivery device (404) in another scheme is connected with syringe piston fully extended such that there is limited free volume within the barrel of the syringe. Then, after expression of material, the syringe plunger is pulled back to allow for expelled material in the catchment area to be drawn into the syringe (404) or other attached delivery device.

Figure 5:
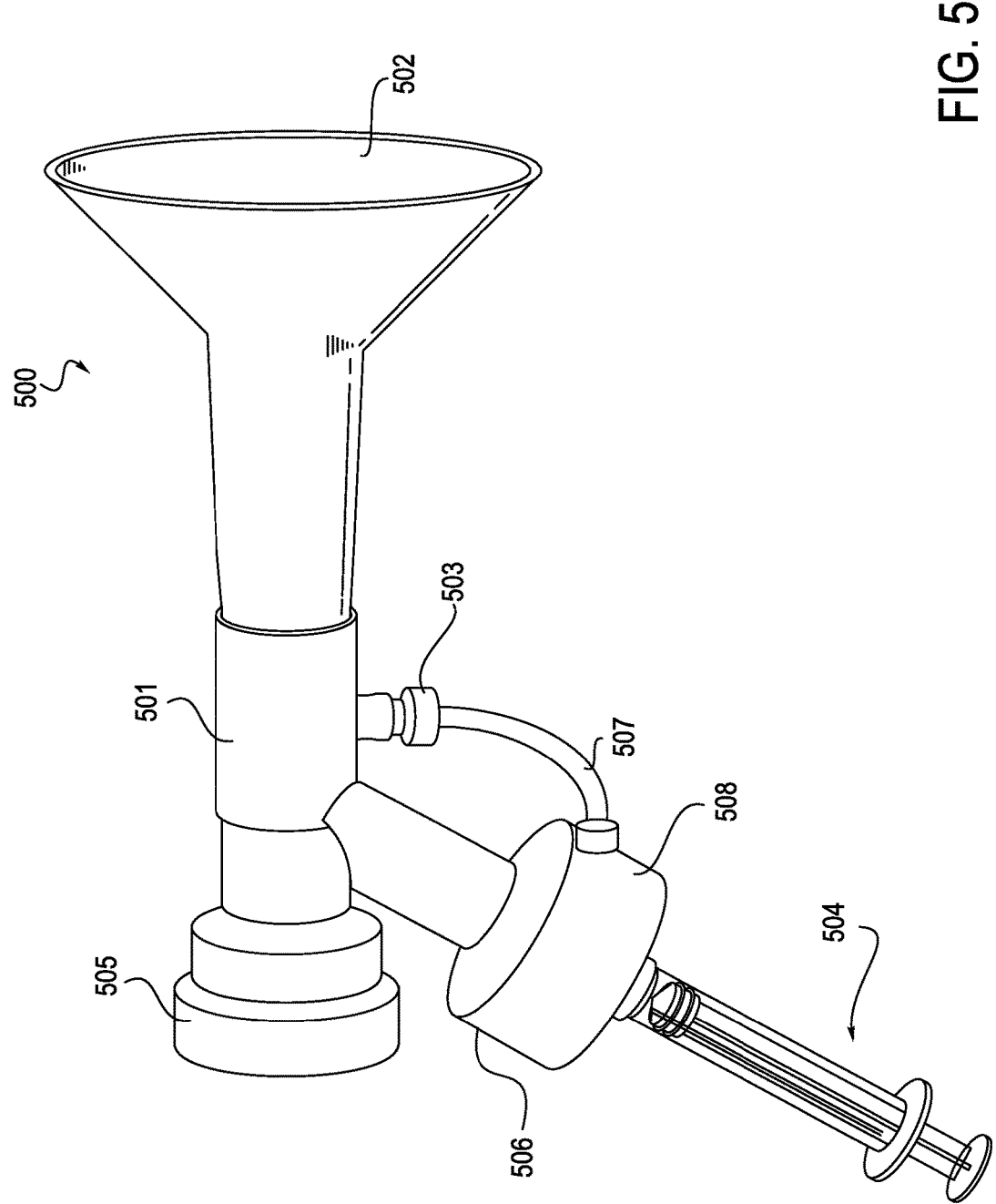
FIG. 5 is a side view of a milk and colostrum collection system with a bypass attachment for small container and dispensing element attachment, according to an alternative embodiment.

FIG. 5 depicts another embodiment of a system (500) that captures and dispenses breast milk and or colostrum. A funnel (502) collects material from a breast or nipple. The material passes through an adaptor (501) to reach a catchment area that facilitates flow to a connector (503) that is in connection with another adaptor (508) by using a bypass tube (507). The bypass tube (507) allows for the suction force to pull pooled material into a delivery device (504) instead of having to go through the one way valve (506) comprised on the connector to the second adaptor (508). There is also a connector for applying a suction or vacuum force (505) constant or pulsatile through the system (500).

Figure 6:
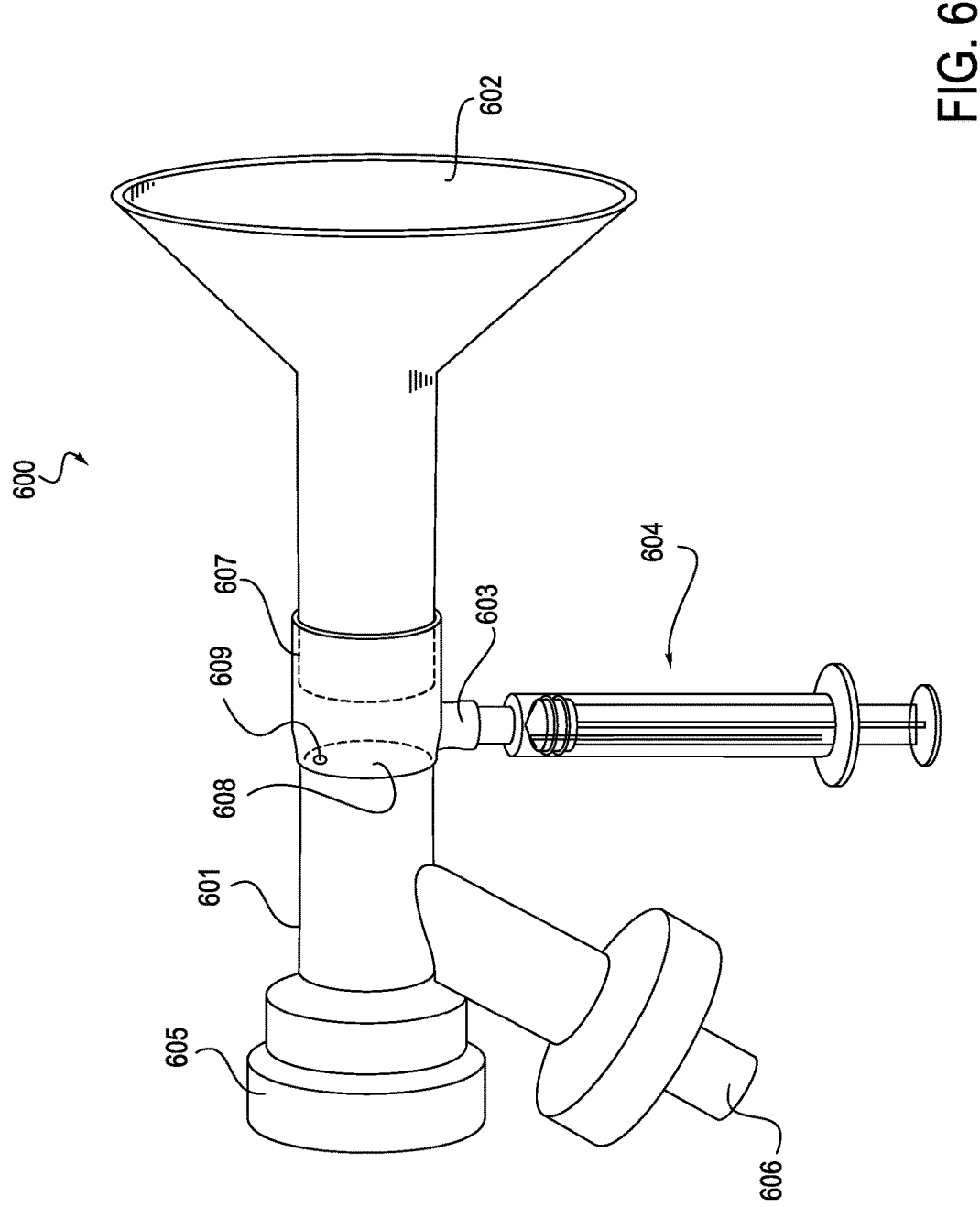
FIG. 6 is a side view of a milk and colostrum collection system, according to another alternative embodiment.

FIG. 6 depicts an exemplary side view of another alternative embodiment of a system (600) to collect and dispense colostrum and/or breast milk. The system (600) includes a one-piece adaptor (601), which includes a central portion that braches into: a port (605) to allow for a flow force, such as vacuum; a one way valve portion (606); a breast shield connection portion (607) for connecting to a breast shield (602) (or "funnel" or "flange"); and a connector (603), for connecting to a colostrum/breast milk collection/delivery device, such as but not limited to a syringe (604) (as illustrated). The adaptor (601), in this embodiment, combines the features of the adaptor (401), port (405) and valve portion (406) of the embodiment illustrated in FIG. 4 in one part. The one-part adaptor (601) may also include an inner wall (608) with a small aperture (609). The inner wall (608) blocks colostrum and/or breast milk expressed from the breast and directs it through the connector (603) into the collection/delivery device (604). The aperture (609) allows suction to be applied via the port (605), through the adaptor (601), to the breast shield (602).

As illustrated in FIG. 6, the breast shield connection portion (607) may comprise a slightly widened, open end of the adaptor (601), sized and configured so that the breast shield (602) may be inserted into it. In some embodiments, the breast shield (602) may fit into the breast shield connection portion (607) via a press fit connection. In alternative embodiments, the breast shield (602) may attach to the breast shield connection portion (607) via threads or any other suitable connection means.

The collection/delivery device (604) may be used to collect small quantities of liquid or more viscous liquid such as but not limited to colostrum, and/or it may be used to periodically sample small quantities from the flow stream into the larger container. In various embodiments, any suitable size of syringe may be used as collection/delivery device (604). Also, as mentioned above, other types of collection/delivery devices may alternatively be used. Additionally, the collection/delivery device (604), if pre-filled with air before attachment, may be used to force air into the breast shield (602) in order to build positive pressure that would facilitate the detachment of the breast from the suction of the breast shield (602) by neutralizing the vacuum force. The collection/delivery device (604), in some embodiments, may be connected with the connector (603) with the syringe piston fully extended, such that there is limited free volume within the barrel of the syringe. Then, after expression of material, the syringe plunger is pulled back to allow for expelled material in the catchment area to be drawn into the syringe (604) or other attached delivery device.

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Modifications and variations are intended to be included within the scope of the application.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications without departing from the scope of the present invention. For instance, the examples, embodiments, geometries, materials, dimensions, ratios, steps, and the like discussed above are illustrative and are not required. Accordingly, the scope of the present invention is not limited to the details of structure and operation shown and described in the specification and drawings.

What is claimed is:

1. A funnel device for use in a system for collecting colostrum from a breast, the funnel device comprising:
 a body, comprising;
  a funnel shaped portion, having a first open end for contacting the breast;
  a cylindrical shaped portion extending from the funnel shaped portion and having a second open end opposite the first open end for connecting to a first source of suction;
  a depression in the cylindrical shaped portion of the body, extending from the funnel shaped portion proximally along the cylindrical shaped portion between the first open end and the second open end; and
  a connector on one end of the depression, for connecting the funnel device to a syringe, wherein the syringe comprises a second source of suction, and wherein the funnel device does not include a valve between the depression and the connector;
 a block inside the cylindrical shaped portion of the body, between the depression and the second open end, for preventing colostrum from passing beyond the depression and through the second open end, wherein the block is oriented perpendicular to a cylindrical wall that forms the cylindrical shaped portion of the body; and
 a vent hole in the block for allowing suction force to be transmitted from the second open end to the first open end.

2. The device as in claim 1, wherein the connector is configured to connect directly to the syringe.

3. The device as in claim 1, wherein the connector is configured to connect to a tube that connects to the syringe.

4. The device as in claim 1, wherein the second open end is configured to attach to a breast pump system.

* * * * *